United States Patent
Abrams et al.

(10) Patent No.: US 11,179,365 B2
(45) Date of Patent: Nov. 23, 2021

(54) PHARMACEUTICAL COMBINATION COMPRISING LSZ102 AND RIBOCICLIB

(71) Applicant: NOVARTIS AG, Basel (CH)

(72) Inventors: Tinya Abrams, Acton, MA (US); Larry Alexander Gaither, Bradford, MA (US)

(73) Assignee: NOVARTIS AG, Basel (CH)

( * ) Notice: Subject to any disclaimer, the term of this patent is extended or adjusted under 35 U.S.C. 154(b) by 217 days.

(21) Appl. No.: 16/190,298

(22) Filed: Nov. 14, 2018

(65) Prior Publication Data

US 2019/0142796 A1 May 16, 2019

Related U.S. Application Data

(60) Provisional application No. 62/587,239, filed on Nov. 16, 2017, provisional application No. 62/758,835, filed on Nov. 12, 2018.

(51) Int. Cl.
| | | |
|---|---|---|
| *A61K 31/381* | (2006.01) | |
| *A61K 31/519* | (2006.01) | |
| *A61P 35/00* | (2006.01) | |
| *A61K 9/00* | (2006.01) | |

(52) U.S. Cl.
CPC .......... *A61K 31/381* (2013.01); *A61K 9/0053* (2013.01); *A61K 31/519* (2013.01); *A61P 35/00* (2018.01)

(58) Field of Classification Search
CPC .. A61K 31/381; A61K 9/0053; A61K 31/519; A61P 35/00
See application file for complete search history.

(56) References Cited

U.S. PATENT DOCUMENTS

| | | |
|---|---|---|
| 10,695,333 B2 | 6/2020 | Abrams et al. |
| 2015/0080483 A1 | 3/2015 | Hanebuth et al. |
| 2016/0375033 A1 | 12/2016 | Edgar |

FOREIGN PATENT DOCUMENTS

| | | |
|---|---|---|
| JP | 2016523253 | 8/2016 |
| WO | WO 2007030360 | 3/2007 |
| WO | WO 2015080438 | 6/2013 |
| WO | 2015022609 A1 | 2/2015 |
| WO | WO 2015028409 | 3/2015 |
| WO | WO 2015/136016 | 9/2015 |
| WO | WO 2016/176666 | 11/2016 |
| WO | 2017168303 A1 | 10/2017 |
| WO | WO 2017/172957 | 10/2017 |
| WO | WO 2018/129387 | 7/2018 |

OTHER PUBLICATIONS

NCT02734615 (first posted Apr. 12, 2016, study start date Jun. 14, 2016).*
Corona, S.P., et al., Advances in Systemic Therapy for Metastatic Cancer, Future Perspectives: Medical Oncology, Science and Technology Letters, vol. 34, No. 7, May 19, 2017, pp. 1-16.
Wardell, Suzanne, E., et al., Efficacy of SERD/SERM Hybrid-CDK4/6 Inhibitor Combinations in Models of Endocrine Therapy-Resistant Breast Cancer, Clinical Cancer Research, An Official Journal of the American Association for Cancer Research, vol. 21, No. 22, Nov. 15, 2015, pp. 5121-5130.
Turner, Nicholas, C., et al., Advances in the Treatment of Advanced Oestrogen-Receptor-Postive Breast Cancer, Lancet, Elsevier, Amsterdam, NL, vol. 389, No. 10087, Dec. 7, 2016, pp. 2403-2414.
Tolaney, S.M., et al., Ribociclib Plus Fulvestrant in Postmenopausal Women with HR+, HER2-Advanced Breast Cancer (ABC), Cancer Research, vol. 77, No. Suppl. 4, Feb. 2017, pp. P4-P22.
Juric, Dejan, et al., Phase I/Ib Study of the SERD LSZ102 Alone or in Combination with Ribociclib in ER Plus Breast Cancer, Cancer Research, vol. 78, No. 4, Suppl. S, Feb. 2018, pp. P5-P21.
Blackburn, Sophie A., et al., Fulvestrant for the Treatment of Advanced Breast Cancer, School of Medicine, University of Nottingham, UK, Expert Review of Anticancer Therapy, (2018), vol. 18 (7), pp. 619-628.
Nichols, Mark, New Directions for Drug-Resistant Breast Cancer, the CDK4/6 Inhibitors, Department of Pharmacology & Chemical Biology, School of Medicine, University of Pittsburgh, PA, Future Medicinal Chemistry (2015), vol. 7(12), pp. 1473-1481.
Weir, Hazel M., et al., AZD9496, An Oral Estrogen Receptor Inhibitor That Blocks the Growth of ER-Positive and ESR-1-Mutant Breast Tumors in Preclinical Models, Astra Zeneca, Oncology iMed, Macclesfield, UK, Cancer Research (2016), vol. 76(11), pp. 3307-3318.
Clinical Cancer Research, 2015, vol. 21(22), pp. 5121-5130.
Expert Review of Anticancer Therapy, 2018, vol. 18(7), pp. 619-628.
Cancer Research, 2016, vol. 76(11), pp. 3307-3318.
Future Medicinal Chemistry, 2015, vol. 7(12), pp. 1473-1481.
Tria, George S et al., Discovery of LSZ102, a Potent, Orally Bioavailable Selective Estrogen Receptor Degrader (SERD) for the Treatment of Estrogen Receptor Positive Breast Cancer, Journal of Medicinal Chemisry, vol. 61, No. 7, Mar. 22, 2018, pp. 2837-2864, XP055564421, US ISSN 0022-2623, DOI 10.1021/acs.

* cited by examiner

*Primary Examiner* — Jared Barsky
(74) *Attorney, Agent, or Firm* — David K. Cheung

(57) ABSTRACT

The present invention relates to a pharmaceutical combination comprising LSZ102 and ribociclib; pharmaceutical compositions comprising the same; and methods of using such combinations and compositions in the treatment or prevention of conditions in which degradation of estrogen receptors combined with CDK4/6 inhibition is beneficial in, for example, the treatment of cancers.

5 Claims, 11 Drawing Sheets

Fulves (Fulvestrant), Tam (Tamoxifen)

PHARMACEUTICAL COMBINATION COMPRISING LSZ102 AND RIBOCICLIB

FIELD OF THE INVENTION

The present invention relates to a pharmaceutical combination comprising LSZ102 and ribociclib; pharmaceutical compositions comprising the same; and methods of using such combinations and compositions in the treatment or prevention of conditions in which degradation of estrogen receptors combined with CDK4/6 inhibition is beneficial, for example, in the treatment of cancers.

BACKGROUND OF THE INVENTION

Estrogens play a critical role in the development of female and male reproductive tissues and contributes to the development and progression of estrogen receptor diseases or disorders such as breast, ovarian, colon, prostate, endometrial and uterine cancers.

Estrogen receptor (ERα)-positive diseases such as breast cancer are usually treated with a selective estrogen receptor modulator (SERM) or an aromatase inhibitor (AI). While these therapies have proven effective at reducing the incidence of progression of breast cancer, some patients exhibit treatment resistance and progress to advanced metastatic breast cancer.

Treatment resistance results, in part, from the evolution of tumors to a state of hypersensitivity to low estrogen levels (AI treatment) or development of dependence upon the antiestrogen for activation of transcription (SERM treatment). SERDs degrade the receptor, effectively eliminating ERα expression and in so doing circumvent the underlying mechanisms of resistance that develop to antiendocrine monotherapy. Further, clinical and preclinical data show that a significant number of the resistance pathways can be circumvented by the use of an antiestrogen that exhibits SERD activity.

Cyclin D proteins are critical in cancer cell division and complex with the CDK4 and CDK6 protein kinases to promote G1 progression by hyperphosphorylating and activating the retinoblastoma protein (pRb). Abnormalities that result in CDK activation are highly enriched in luminal A and B breast cancer subtypes, ~85% of which are ER+/HER2−. The luminal subtypes also maintain expression of pRb, which is essential for benefit from treatment with a CDK4/6 inhibitor. ER+ breast cancer cell lines are among the cancer models most sensitive to single agent CDK4/6 inhibition as well as to the combination of endocrine therapy and CDK4/6 inhibition.

The combination of the present invention, LSZ102 and ribociclib, can be used as therapies for the treatment of estrogen receptor diseases or disorders, for example, ovulatory dysfunction, uterine cancer, endometrium cancer, ovarian cancer, endometriosis, osteoporosis, prostate cancer, benign prostatic hypertrophy, estrogen receptor alpha (ERα)-positive breast cancer, in particular ERα-positive breast cancer exhibiting de novo resistance to existing anti-estrogens and aromatase inhibitors.

SUMMARY OF THE INVENTION

The present invention provides for a pharmaceutical combination comprising:

(a) (E)-3-(4-((2-(2-(1,1-difluoroethyl)-4-fluorophenyl)-6-hydroxybenzo[b]thiophen-3-yl)oxy)phenyl)acrylic acid (LSZ102), or a pharmaceutically acceptable salt thereof, having the structure:

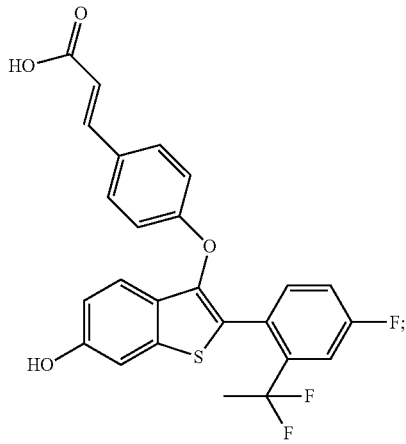 [SMILES: CC(F)(F)c1cc(F)ccc1-c1sc2cc(O)ccc2c1Oc1ccc(/C=C/C(=O)O)cc1]

and (b) 7-cyclopentyl-N,N-dimethyl-2-((5-(piperazin-1-yl)pyridin-2-yl)amino)-7H-pyrrolo[2,3-d]pyrimidine-6-carboxamide (ribociclib), or a pharmaceutically acceptable salt thereof, having the structure:

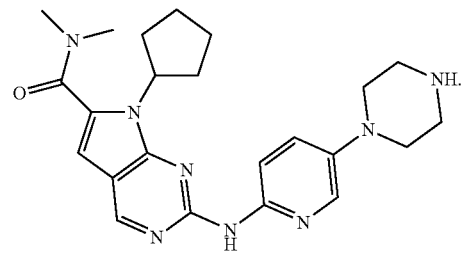 [SMILES: CN(C)C(=O)c1cc2cnc(Nc3ccc(N4CCNCC4)cn3)nc2n1C1CCCC1]

Combinations of LSZ102, or a pharmaceutically acceptable salt thereof, and ribociclib, or a pharmaceutically acceptable salt thereof, will also be referred to herein as a "combination of the invention".

In another embodiment of the combination of the invention, LSZ102 or a pharmaceutically acceptable salt thereof and ribociclib, or a pharmaceutically acceptable salt thereof, are in the same formulation.

In another embodiment of the combination of the invention, LSZ102 or a pharmaceutically acceptable salt thereof and ribociclib or a pharmaceutically acceptable salt thereof are in separate formulations.

In another embodiment, the combination of the invention is for simultaneous or sequential (in any order) administration. The combination can be administered in a single dosage formulation or in separate dosage formulations.

In another embodiment is a method for treating or preventing cancer in a subject in need thereof comprising administering to the subject a therapeutically effective amount of the combination of the invention.

In a further embodiment of the method, the cancer is estrogen receptor alpha (ERα) positive breast cancer.

In a further embodiment of the method, the cancer is selected from ovarian, endometrial, prostate, uterine, cervical and lung cancers.

In a further embodiment, the combination of the invention provides for a use in the manufacture of a medicament for treating estrogen receptor alpha (ERα) positive breast cancer.

In a further embodiment, the combination of the invention provides for a use in the manufacture of a medicament for treating a cancer selected from ovarian, endometrial, prostate, uterine, cervical and lung cancers.

In another embodiment is a pharmaceutical composition comprising the combination of the invention.

In a further embodiment, the pharmaceutical composition further comprises one or more pharmaceutically acceptable excipients.

DEFINITIONS

Figure 1:
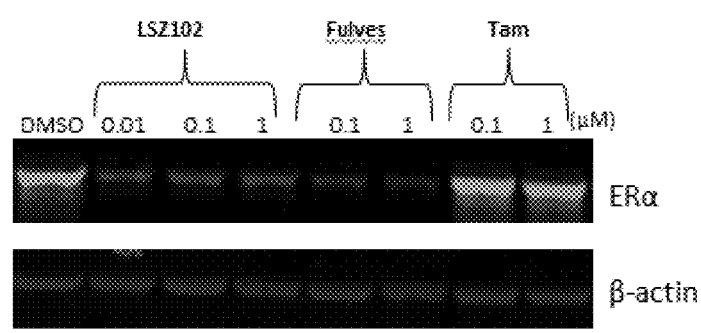
FIG. 1: Comparison of LSZ102, fulvestrant and tamoxifen on the promotion of ER degradation in MCF-7 cells.

The general terms used hereinbefore and hereinafter preferably have within the context of this disclosure the following meanings, unless otherwise indicated, where more general terms wherever used may, independently of each other, be replaced by more specific definitions or remain, thus defining more detailed embodiments of the invention:

"ESR1 mutations" are estrogen receptor gene (ESR1) mutations. Mutations result in ligand independent ER activity. Several mutations have been identified that modify the ligand binding domain of the ER. These mutations include, but are not limited to, D538G, E380Q and Y537S/N/C, representing more than 80% of the ESR1 mutations. These mutations are an acquired molecular event since they are almost absent in primary BC tumor (<2%). ESR1 mutations are common in patients who have received aromatase inhibitors in a metastatic setting. Mutations occur in 9% of early metastatic ER+ disease (Y537N/S and D538G) and 20% in late metastatic ER+ breast cancer (Y537C/N/S and D538G). Compared to wild-type, tumor growth is higher with D538G and Y537S mutations.

The term "subject" or "patient" as used herein is intended to include animals, which are capable of suffering from or afflicted with a cancer or any disorder involving, directly or indirectly, a cancer. Examples of subjects include mammals, e.g., humans, apes, monkeys, dogs, cows, horses, pigs, sheep, goats, cats, mice, rabbits, rats, and transgenic non-human animals. In an embodiment, the subject is a human, e.g., a human suffering from, at risk of suffering from, or potentially capable of suffering from cancers.

The term "treating" or "treatment" as used herein comprises a treatment relieving, reducing or alleviating at least one symptom in a subject or effecting a delay of progression of a disease. For example, treatment can be the diminishment of one or several symptoms of a disorder or complete eradication of a disorder, such as cancer. Within the meaning of the present disclosure, the term "treat" also denotes to arrest, delay the onset (i.e., the period prior to clinical manifestation of a disease) and/or reduce the risk of developing or worsening a disease.

The terms "comprising" and "including" are used herein in their open-ended and non-limiting sense unless otherwise noted.

The terms "a" and "an" and "the" and similar references in the context of describing the invention (especially in the context of the following claims) are to be construed to cover both the singular and the plural, unless otherwise indicated herein or clearly contradicted by context. Where the plural form is used for compounds, salts, and the like, this is taken to mean also a single compound, salt, or the like.

The term "synergistic effect" as used herein refers to action of two therapeutic agents such as, for example, a compound LSZ102 as a selective estrogen receptor modulator and ribociclib as a CDK4/6 inhibitor, producing an effect, for example, slowing the symptomatic progression of a proliferative disease, particularly cancer, or symptoms thereof, which is greater than the simple addition of the effects of each drug administered by themselves. A synergistic effect can be calculated, for example, using suitable methods such as the Sigmoid-Emax equation (Holford, N. H. G. and Scheiner, L. B., Clin. Pharmacokinet. 6: 429-453 (1981)), the equation of Loewe additivity (Loewe, S. and Muischnek, H., Arch. Exp. Pathol Pharmacol. 114: 313-326 (1926)) and the median-effect equation (Chou, T. C. and Talalay, P., Adv. Enzyme Regul. 22: 27-55 (1984)). Each equation referred to above can be applied to experimental data to generate a corresponding graph to aid in assessing the effects of the drug combination. The corresponding graphs associated with the equations referred to above are the concentration-effect curve, isobologram curve and combination index curve, respectively.

The combination of the invention, LSZ102 and ribociclib, is also intended to represent unlabeled forms as well as isotopically labeled forms of the compounds. Isotopically labeled compounds have one or more atoms replaced by an atom having a selected atomic mass or mass number. Examples of isotopes that can be incorporated into LSZ102 and ribociclib include isotopes of hydrogen, carbon, nitrogen, oxygen, phosphorous, fluorine, and chlorine, such as $^2H$, $^3H$, $^{11}C$, $^{13}C$, $^{14}C$, $^{15}N$, $^{18}F$ $^{31}F$, $^{32}F$, $^{35}S$, $^{36}Cl$, $^{123}I$, $^{124}I$, $^{125}I$ respectively. The invention includes isotopically labeled LSZ102 and ribociclib, for example into which radioactive isotopes, such as $^3H$ and $^{14}C$, or non-radioactive isotopes, such as $^2H$ and $^{13}C$, are present. Isotopically labelled LSZ102 and ribociclib are useful in metabolic studies (with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, LSZ102 labeled with $^{18}$F may be particularly desirable for PET or SPECT studies. Isotopically-labeled compounds of the invention can generally be prepared by conventional techniques known to those skilled in the art or by processes analogous to those described in the accompanying Examples using appropriate isotopically-labeled reagents.

Further, substitution with heavier isotopes, particularly deuterium (i.e., $^2$H or D) may afford certain therapeutic advantages resulting from greater metabolic stability, for example increased in vivo half-life or reduced dosage requirements or an improvement in therapeutic index. It is understood that deuterium in this context is regarded as a substituent of either LSZ102 or ribociclib. The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in LSZ102 or ribociclib is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

DESCRIPTION OF PREFERRED EMBODIMENTS

LSZ102 is an investigational agent that is an orally bioavailable small molecule that has mixed SERD and SERM activity, with both anti-estrogenic and pro-estrogenic effects in animals. In breast cancer cell lines in vitro, LSZ102 has shown potent ER antagonism and degradation activity.

In one embodiment, with respect to the pharmaceutical combination of the invention, is a pharmaceutical combination comprising (E)-3-(4-((2-(2-(1,1-difluoroethyl)-4-fluorophenyl)-6-hydroxybenzo[b]thiophen-3-yl)oxy)phenyl) acrylic acid, or pharmaceutically acceptable salt thereof, and 7-cyclopentyl-N,N-dimethyl-2-((5-(piperazin-1-yl)pyridin-2-yl)amino)-7H-pyrrolo[2,3-d]pyrimidine-6-carboxamide, or a pharmaceutically acceptable salt thereof.

In a further embodiment, (E)-3-(4-((2-(2-(1,1-difluoroethyl)-4-fluorophenyl)-6-hydroxybenzo[b]thiophen-3-yl)oxy)phenyl)acrylic acid, or a pharmaceutically acceptable salt thereof, and 7-cyclopentyl-N,N-dimethyl-2-((5-(piperazin-1-yl)pyridin-2-yl)amino)-7H-pyrrolo[2,3-d]pyrimidine-6-carboxamide, or a pharmaceutically acceptable salt thereof, are administered separately, simultaneously or sequentially, in any order.

In a further embodiment, the pharmaceutical combination is for oral administration.

In a further embodiment, (E)-3-(4-((2-(2-(1,1-difluoroethyl)-4-fluorophenyl)-6-hydroxybenzo[b]thiophen-3-yl)oxy)phenyl)acrylic acid is in an oral dose form.

In a further embodiment, 7-cyclopentyl-N,N-dimethyl-2-((5-(piperazin-1-yl)pyridin-2-yl)amino)-7H-pyrrolo[2,3-d]pyrimidine-6-carboxamide is in an oral dose form.

In another embodiment, is a pharmaceutical composition comprising a pharmaceutical combination of (E)-3-(4-((2-(2-(1,1-difluoroethyl)-4-fluorophenyl)-6-hydroxybenzo[b]thiophen-3-yl)oxy)phenyl)acrylic acid, or pharmaceutically acceptable salt thereof, and 7-cyclopentyl-N,N-dimethyl-2-((5-(piperazin-1-yl)pyridin-2-yl)amino)-7H-pyrrolo[2,3-d]pyrimidine-6-carboxamide, or a pharmaceutically acceptable salt thereof and at least one pharmaceutically acceptable carrier.

In a further embodiment, is a pharmaceutical combination of (E)-3-(4-((2-(2-(1,1-difluoroethyl)-4-fluorophenyl)-6-hydroxybenzo[b]thiophen-3-yl)oxy)phenyl)acrylic acid, or pharmaceutically acceptable salt thereof, and 7-cyclopentyl-N,N-dimethyl-2-((5-(piperazin-1-yl)pyridin-2-yl)amino)-7H-pyrrolo[2,3-d]pyrimidine-6-carboxamide, or a pharmaceutically acceptable salt thereof, for use in the treatment of wild-type ER+ breast cancer.

In another embodiment, is a pharmaceutical combination of (E)-3-(4-((2-(2-(1,1-difluoroethyl)-4-fluorophenyl)-6-hydroxybenzo[b]thiophen-3-yl)oxy)phenyl)acrylic acid, or pharmaceutically acceptable salt thereof, and 7-cyclopentyl-N,N-dimethyl-2-((5-(piperazin-1-yl)pyridin-2-yl)amino)-7H-pyrrolo[2,3-d]pyrimidine-6-carboxamide, or a pharmaceutically acceptable salt thereof, for use in the treatment of ESR1 mutant ER+ breast cancer.

In a further embodiment, the ESR1 mutation is a MCR7 expressing ESR1 mutation.

In a further embodiment, the ESR1 mutations are selected from the group consisting of D538G, E380Q, Y537S, Y537N and Y537C.

In a further embodiment, the ESR1 mutations are selected from the group consisting of D538G and Y537S.

In another embodiment, is a use of the pharmaceutical combination of (E)-3-(4-((2-(2-(1,1-difluoroethyl)-4-fluorophenyl)-6-hydroxybenzo[b]thiophen-3-yl)oxy)phenyl) acrylic acid, or pharmaceutically acceptable salt thereof, and 7-cyclopentyl-N,N-dimethyl-2-((5-(piperazin-1-yl)pyridin-2-yl)amino)-7H-pyrrolo[2,3-d]pyrimidine-6-carboxamide, or a pharmaceutically acceptable salt thereof, for the manufacture of a medicament for the treatment of ER+ breast cancer.

In another embodiment, is a method of treating wild-type ER+ breast cancer comprising administrating to a patient in need thereof a pharmaceutical combination of (E)-3-(4-((2-(2-(1,1-difluoroethyl)-4-fluorophenyl)-6-hydroxybenzo[b]thiophen-3-yl)oxy)phenyl)acrylic acid, or pharmaceutically acceptable salt thereof, and 7-cyclopentyl-N,N-dimethyl-2-((5-(piperazin-1-yl)pyridin-2-yl)amino)-7H-pyrrolo[2,3-d]pyrimidine-6-carboxamide, or a pharmaceutically acceptable salt thereof, or a pharmaceutical composition comprising a pharmaceutical combination of (E)-3-(4-((2-(2-(1,1-difluoroethyl)-4-fluorophenyl)-6-hydroxybenzo[b]thiophen-3-yl)oxy)phenyl)acrylic acid, or pharmaceutically acceptable salt thereof, and 7-cyclopentyl-N,N-dimethyl-2-((5-(piperazin-1-yl)pyridin-2-yl)amino)-7H-pyrrolo[2,3-d]pyrimidine-6-carboxamide, or a pharmaceutically acceptable salt thereof and at least one pharmaceutically acceptable carrier.

In another embodiment, is a method of treating ER+ breast cancer, wherein said ER+ breast cancer contains ESR1 mutations, comprising administrating to a patient in need thereof a pharmaceutical combination of (E)-3-(4-((2-(2-(1,1-difluoroethyl)-4-fluorophenyl)-6-hydroxybenzo[b]thiophen-3-yl)oxy)phenyl)acrylic acid, or pharmaceutically acceptable salt thereof, and 7-cyclopentyl-N,N-dimethyl-2-((5-(piperazin-1-yl)pyridin-2-yl)amino)-7H-pyrrolo[2,3-d]pyrimidine-6-carboxamide, or a pharmaceutically acceptable salt thereof, or a pharmaceutical composition comprising a pharmaceutical combination of (E)-3-(4-((2-(2-(1,1-difluoroethyl)-4-fluorophenyl)-6-hydroxybenzo[b]thiophen-3-yl)oxy)phenyl)acrylic acid, or pharmaceutically acceptable salt thereof, and 7-cyclopentyl-N,N-dimethyl-2-((5-(piperazin-1-yl)pyridin-2-yl)amino)-7H-pyrrolo[2,3-d]pyrimidine-6-carboxamide, or a pharmaceutically acceptable salt thereof and at least one pharmaceutically acceptable carrier.

In a further embodiment, the mutations are selected from the group consisting of D538G, E380Q, Y537S, Y537N and Y537C.

In a further embodiment, the mutations are selected from D538G and Y537S.

In another embodiment, (E)-3-(4-((2-(2-(1,1-difluoroethyl)-4-fluorophenyl)-6-hydroxybenzo[b]thiophen-3-yl)oxy)phenyl)acrylic acid is administered orally at a dose of about 100 mg per day, or 200 mg per day, or 300 mg per day, or 400 mg per day, or 500 mg per day, or 600 mg per day.

In a further embodiment, 7-cyclopentyl-N,N-dimethyl-2-((5-(piperazin-1-yl)pyridin-2-yl)amino)-7H-pyrrolo[2,3-d]pyrimidine-6-carboxamide is administered orally at a dose of about 100 mg per day, or 200 mg per day, or 300 mg per day, or 400 mg per day, or 500 mg per day, or 600 mg per day.

In a further embodiment, 7-cyclopentyl-N,N-dimethyl-2-((5-(piperazin-1-yl)pyridin-2-yl)amino)-7H-pyrrolo[2,3-d]pyrimidine-6-carboxamide is administered orally at a dose of about 100 mg per day, or 200 mg per day, or 300 mg per day, or 400 mg per day, or 500 mg per day, or 600 mg per day, continuously.

In a further embodiment, 7-cyclopentyl-N,N-dimethyl-2-((5-(piperazin-1-yl)pyridin-2-yl)amino)-7H-pyrrolo[2,3-d]pyrimidine-6-carboxamide is administered orally at a dose of about 100 mg per day, or 200 mg per day, or 300 mg per day, or 400 mg per day, or 500 mg per day, or 600 mg for 21 days followed by 7 days off treatment.

In a further embodiment, 7-cyclopentyl-N,N-dimethyl-2-((5-(piperazin-1-yl)pyridin-2-yl)amino)-7H-pyrrolo[2,3-d]pyrimidine-6-carboxamide is administered orally at 600 mg for 21 days followed by 7 days off treatment.

Pharmacology and Utility

Breast cancer is a leading cause of cancer mortality among women. Though often generalized as a single disease, breast cancer is more commonly classified in a clinical setting by its molecular subtype, arising from the characterization of three key biomarkers. The presence or absence of the receptors estrogen and progesterone lead to a hormone receptor classification (HR+/HR−) while increased or decreased levels of the human epidermal growth factor receptor 2 (HER2) lead to a HER2 protein classification (HER2+/HER2−). Nearly 74% of breast cancers demonstrate high expression of the estrogen receptor-α (ERα), a nuclear hormone receptor directly implicated in the progression of HR+ cancers. This ligand-inducible transcription factor binds the hormone estrogen to activate and promote the expression of oncogenic genes.

In patients with ERα positive breast cancer treatment has long relied on endocrine therapies such as tamoxifen (and its active metabolite, 4-hydroxytamoxifen) and anastrozole, both of which prevent ligand activation and ultimately gene expression. Tamoxifen, the primary standard of care for such patients, functions as an estrogen receptor modulator effectively blocking the binding of estrogen to the receptor and blocking its effects in breast tissue. Women treated with this first-line therapy often respond positively and show increased survival in clinical settings, but acquired resistance in these patients, ultimately leading to disease relapse, remains a significant medical challenge. Though the specific mechanism through which ERα positive tumors develop resistance to tamoxifen is not fully understood, aromatase inhibitors, such as letrazole have shown clinical efficacy in such refractory cancers. In contrast to tamoxifen, aromatase inhibitors owe their activity to the reduction in estrogen production, more specifically by inhibiting the enzyme responsible for the key biosynthetic step in the formation of estrogen. Unfortunately, as with tamoxifen, aromatase inhibitors can also lead to resistant cancer.

Fulvestrant is a selective estrogen receptor degrader (SERD) approved for treatment of endocrine resistant cancer. This steroid-based anti-estrogen both binds and accelerates the degradation of the estrogen receptor and is clinically effective in endocrine treated patients whose disease has progressed. Fulvestrant is limited, however, in its clinical utility owing in large part to its poor physicochemical properties. The drug cannot be administered orally but instead the approved clinical dosage of 500 mg administered into the gluteal area in two 5 mL injections once-monthly, does not appear sufficient to fully occupy the receptor. LSZ102 was developed as an oral medication, with improved bioavailability while retaining desirable estrogen receptor degradative properties.

The introduction of CDK4/6 inhibitors into the treatment of ER+ breast cancer was supported by strong preclinical data and rationale. Cyclin D proteins are critical in cancer cell division and complex with the CDK4 and CDK6 protein kinases to promote G1 progression by hyperphosphorylating and activating the retinoblastoma protein (pRb). Abnormalities that result in CDK activation are highly enriched in luminal A and B breast cancer subtypes, ~85% of which were ER+/HER2−. The luminal subtypes also maintain expression of pRb, which is essential for benefit from treatment with a CDK4/6 inhibitor. ER+ breast cancer cell lines are among the cancer models most sensitive to single agent CDK4/6 inhibition as well as to the combination of endocrine therapy and CDK4/6 inhibition.

On the basis of the inhibitory studies described in the "Examples" section below, the combination of LSZ102 and ribociclib shows therapeutic efficacy. Example 8 details the efficacy of LSZ102 and ribociclib as a combination, tested in the orthotopic MCF-7 breast cancer model in mice. Single agent treatments of LSZ102 at 10 mg/kg QD and ribociclib at 75 mg/kg QD resulted in a tumor growth inhibition (%ΔT/ΔC of 10% and 19%, respectively. Surprisingly, the combination of the two induced a 28% tumor regression (Table 7).

Pharmaceutical Compositions

In another aspect, the present invention provides pharmaceutically acceptable compositions which comprise a therapeutically-effective amount LSZ102 and ribociclib, formulated together with one or more pharmaceutically acceptable carriers (additives) and/or diluents. As described in detail below, the pharmaceutical compositions of the present invention may be specially formulated for administration in solid or liquid form, including those adapted for oral administration, for example, drenches (aqueous or non-aqueous solutions or suspensions), tablets, e.g., those targeted for buccal, sublingual, and systemic absorption, boluses, powders, granules, pastes for application to the tongue.

The phrase "therapeutically-effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

As set out above, certain embodiments of the present compounds may contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ in the administration vehicle or the dosage form manufacturing process, or by separately reacting a purified compound of the invention in its free base form with a suitable organic or inorganic acid, and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", *J. Pharm. Sci.* 66:1-19).

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like. The pharmaceutically acceptable salt of, for example ribociclib, is succinate.

In other cases, the compounds of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al., supra)

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred per cent, this amount will range from about 0.1 percent to about ninety-nine percent of active ingredient, preferably from about 5 percent to about 70 percent, most preferably from about 10 percent to about 30 percent.

In certain embodiments, a formulation of the present invention comprises an excipient selected from the group consisting of cyclodextrins, celluloses, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution, suspension or solid dispersion in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules, trouches and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions.

When the compounds of the present invention are administered as pharmaceuticals, to humans and animals, they can be given per se or as a pharmaceutical composition containing, for example, 0.1 to 99% (more preferably, 10 to 30%) of active ingredient in combination with a pharmaceutically acceptable carrier.

The compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of the combination of the invention will be that amount of each compound which is the lowest dose effective to produce a therapeutic effect. Such an effective dose will generally depend upon the factors described above.

In another aspect, the present invention provides pharmaceutically acceptable compositions which comprise a therapeutically-effective amount of one or more of the subject compounds, as described above, formulated together with one or more pharmaceutically acceptable carriers (additives) and/or diluents.

EXAMPLES

LSZ102 and Ribociclib (E)-3-(4-((2-(2-(1,1-difluoroethyl)-4-fluorophenyl)-6-hydroxybenzo[b]thiophen-3-yl)oxy)phenyl)acrylic acid (LSZ102) is synthesized according to example 139 of WO2014/130310. 7-cyclopentyl-N,N-dimethyl-2-((5-(piperazin-1-yl)pyridin-2-yl)amino)-7H-pyrrolo[2,3-d]pyrimidine-6-carboxamide (ribociclib) is synthesized according to example 74 of WO2010/020675.

The utility of LSZ102 and ribociclib described herein can be evidenced by testing in the following examples.

Example 1

LSZ102 Promotes ER Degradation in MCF-7 Cells

Western blot. For the analysis of LSZ102, fulvestrant, and tamoxifen on ERα protein levels in MCF-7 tumors at the end of efficacy study, snap frozen tumors were pulverized into a powder and then transferred to Lysing Matrix Tubes (MP Biomedicals Cat. #6913-500) mixed with cold lysis buffer (1× cell lysis buffer; Cell Signaling, Cat. #9803S) containing Complete Mini (1 tablet to 10 mL), PhosStop (1 tablet to 10 mL and 1 M Urea) homogenized by a Fast Prep 24 Tissue Lyser (MP Biomedicals). Total protein concentrations of the lysate were tested by BCA assay (Pierce BCA Protein Assay Kit, Prod #23225, Thermo Scientific) according to the manufacturer's instructions. Lysates were separated by SDS-PAGE, transferred onto membranes, and then immunoblotted using an anti-ERα antibody (Santa Cruz Biotechnology, HC-20), as well as an anti-tubulin antibody as a loading control. Western blots were scanned for quantification of the immunoblotted bands. The percent of ERα remaining was determined by comparing tumors from the treated mice versus those from the vehicle control group. FIG. 1 demonstrates that LSZ102 promotes ER degradation in MCF-7 cells in comparison to fulvestrant and tamoxifen, ER degradation by LSZ102 is similar to fulvestrant at equivalent concentrations, and no effect on ER degradation was observed with tamoxifen in MCF-7 cells.

MCF-7 proliferation assay. Growth factors depleted MCF-7 cells were seeded (10,000 cells/well) in 96-well plates in CSS medium. After overnight incubation, cells were treated with compounds in the presence of estradiol (0.1 nM) for 6 days. The cell viability were then measured by CellTiterGlo assay (Promega).

In the cell proliferation assays, LSZ102 inhibited the growth of MCF-7 cells with an IC50 of 0.7 nM and had no effect on growth of ER-MDA-MB468 cells at 10 µM, suggesting that even at high doses, LSZ102 did not affect the cells lacking ER. LSZ102 is a potent SERD, as demonstrated using a growth factor driven proliferation assay, where insulin and not estrogen drives the cell proliferation. This assay is unaffected by the SERM tamoxifen but is inhibited by the SERD fulvestrant. In the insulin driven proliferation assay using MCF-7 cell line, LSZ102 blocked the cell growth with IC50 of 6 nM, better than fulvestrant.

Example 2

LSZ102 Anti-Proliferation and ER Degradation Activity in MCF-7 Parental and Y537S Cells The effects of LSZ102, fulvestrant, and tamoxifen as single agents were studied in MCF-7 parental (wildtype, or WT) and Y537S mutant cells. MCF-7 WT cells and Y537S mutant cells were incubated in RPMI (without phenol red) plus 10% charcoal dextran-stripped serum and treated with escalated concentration of compounds in the presence of 0.1 nM estradiol (WT) or no estradiol (Y537S). Cell viability was determined by CellTiter-Glo (CTG) assay after 7 days of compound treatment. For ERE-luciferase assay, cell luciferase signal was measured using Bright-Glo assay after 24 hours. IC50 is the compound concentration which inhibits 50% of the CTG signal by 50%. IC50 nanomolar (nM) values were calculated using the XLfit software and are defined as the inflection point of the fitted inhibition curves. The results for anti-proliferation activity of LSZ102, fulvestrant, and tamoxifen in MCF-7 WT and Y537S mutant cells are presented in Table 1.

TABLE 1

| Compound | MCF-7 proliferation Ave IC50 (nM) | |
|---|---|---|
| | ESR1 WT | ESR1 Y537S |
| LSZ102 | 5.2 +/− 0.5 | 27.0 +/− 5.1 |
| Fulvestrant | 2.6 +/− 0.2 | 53.0 +/− 11.9 |
| Tamoxifen | 4.5 +/− 1.0 | 60.1 +/− 10.4 |

In MCF-7 WT cells, the inhibition of cell proliferation by LSZ102, fulvestrant, and tamoxifen was similar. LSZ102 was found to inhibit cell proliferation in MCF-7 WT cells at an IC50 of 5.2 nM while fulvestrant inhibited cell proliferation at 2.6 nM and tamoxifen at 4.5 nM. In MCF-7 Y537S mutant cells, the inhibition of cell proliferation with LSZ102 was the most potent of the three. LSZ102 was found to inhibit cell proliferation in MCF-7 Y537S mutant cells at an IC50 of 27.0 nM while fulvestrant inhibited cell proliferation at 53.0 nM and tamoxifen at 60.1 nM. While all three compounds had a shift in IC50 efficacy from the MCF-7 WT to the Y537S mutant, LSZ102 was the least shifted and retained the most potent activity of the three compounds tested.

Figure 2A:
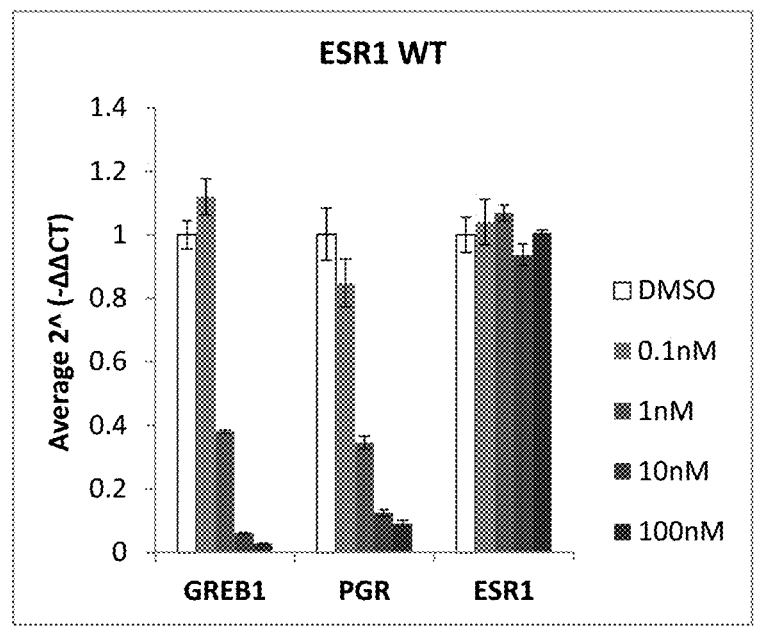
FIG. 2A: PCR analysis of mRNA in LSZ102-treated MCF-7 parental (WT) cells.
Figure 2B:
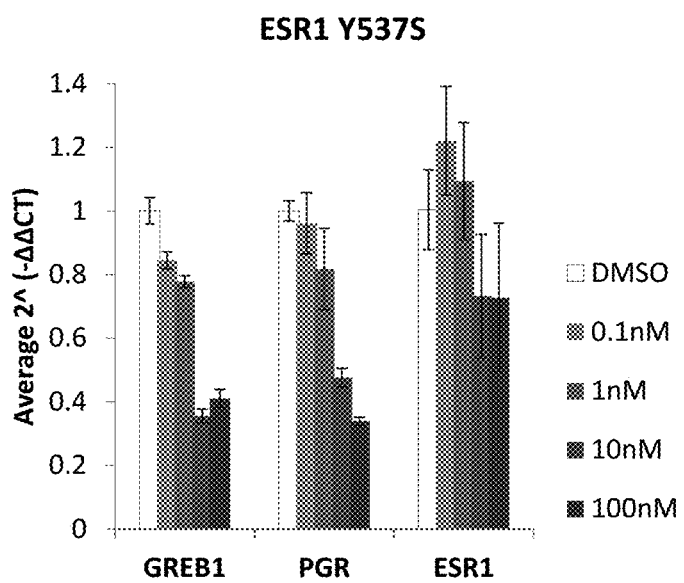
FIG. 2B: PCR analysis of mRNA in LSZ102-treated MCF-7 Y537S mutant cells.

PCR analysis. mRNA from LSZ102-treated MCF-7 WT and Y537S mutant cells were isolated and subjected to qRT-PCR analysis for ER target genes expression (FIGS. 2A and 2B). The mRNA levels of canonical ER target genes GREB1 and PGR were measured against mRNA expression of ER (ESR1), as a control for LSZ102's effect on ER itself, to ensure that the effects are not due to effects on ER mRNA levels but instead on ER protein levels. LSZ102 exhibited a dose response inhibition for the mRNA expression of both GREB1 and PGR in the MCF-7 WT and Y537S mutant cells. The effect was more pronounced in the WT cells, but at high concentrations, GREB1 and PGR expression were significantly reduced. In contrast, ESR1 mRNA levels was not significantly reduced in either cell line.

Figure 3:
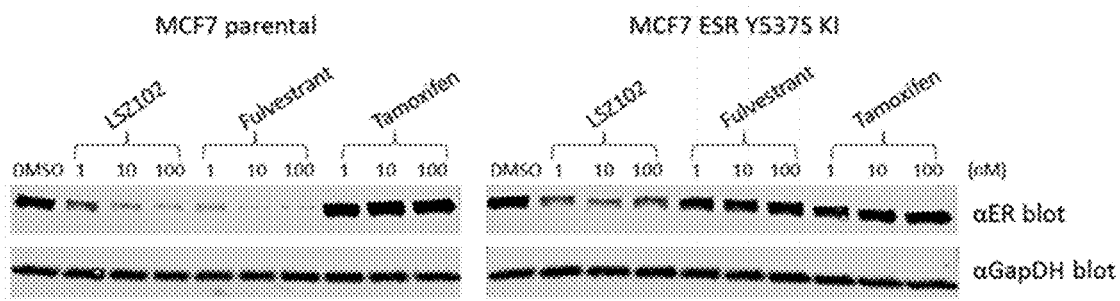
FIG. 3: Comparison of ERα degradation activity of LSZ102, fulvestrant and tamoxifen in MCF-7 parental (WT) and Y537S mutant cells.

Immunoblot analysis. MCF-7 parental and Y537S mutant cells were grown in phenol red free RPMI media with 10% charcoal dextran stripped serum continuously (Y537S mutant) or for 3 days (parental) followed with 24 hr treatment with LSZ102, fulvestrant, and tamoxifen as single agents. Extracted cell lysates were subjected to immunoblot analysis (FIG. 3) for ERα protein quantification. In the MCF-7 parental cells, both LSZ102 and fulvestrant significantly reduce ER protein levels over a dose response. In the MCF-7 Y537S mutant cells, LSZ102 dramatically reduced ER protein levels across doses but fulvestrant did not appear to have any effect.

Example 3

MCF-7 Xenograft Model in NSG Mice

The estrogen response ER positive (ER+) MCF-7 cell line was shown to be sensitive to LSZ102 in vitro. To demonstrate targeted anti-tumor activity in orthotopic MCF-7 xenograft model in NOD scid gamma (NSG) mice, 1, 3, 10 and 20 mg/kg of LSZ102 was administered orally (PO) once daily (QD) along with 5 mg of fulvestrant administered subcutaneously (SC) once weekly (Qweek) per mouse and 60 mg/kg of tamoxifen administered orally (PO) once daily for 5 days per week as positive controls. Mice were supplemented with estradiol (0.72 mg estradiol/90-day release pellets) to further support MCF-7 tumor growth several days prior to cell implantation. MCF-7 tumors were established in female NSG mice by injection of 10×10$^6$ cells in 50% Matrigel® into the axillary mammary fat pad area of each mouse. When tumors reached an average of 200 mm$^3$, mice were randomized according to tumor volume into treatment groups (n=8). The effect of the treatments on tumor response in the MCF-7 breast cancer xenograft model on Day 48 are presented in Table 2.

TABLE 2

| | | Tumor response | |
|---|---|---|---|
| Compound | Dose, Schedule | ΔT/ΔC (%) | Regression (%) |
| Vehicle | None PO, QD | 100 | — |
| LSZ102 | 1 mg/kg, PO, QD | 56 | — |
| LSZ102 | 3 mg/kg, PO, QD | 51 | — |
| LSZ102 | 10 mg/kg, PO, QD | 25* | — |
| LSZ102 | 20 mg/kg, PO, QD | 2* | — |
| Tamoxifen | 60 mg/kg, PO, QD × 5 days × QWeek | −0.8* | 1* |
| Fulvestrant | 5 mg/mouse SC, QWeek | 24* | — |

*p < 0.05 versus vehicle (One-way ANOVA/Holm-Sidak post-hoc test)

Figure 4:
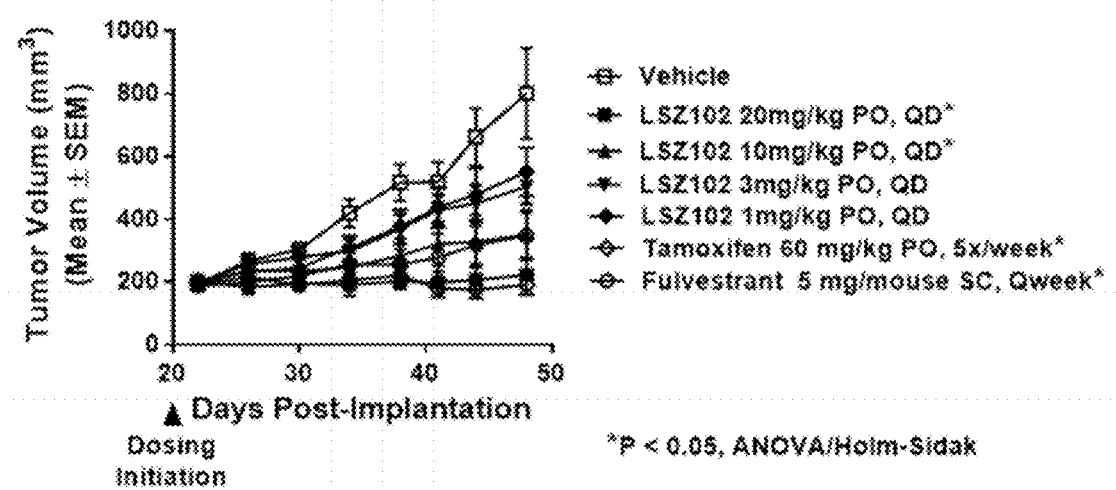
FIG. 4: Anti-tumor efficacy of LSZ102, fulvestrant and tamoxifen in the orthotopic human breast cancer MCF-7 xenograft model.

LSZ102 treatment resulted in dose dependent anti-tumor efficacy (FIG. 4) with maximal activity observed in mice, treated with the dose of 20 mg/kg QD, corresponding to a percentage of mean change in tumor volume vs control (ΔT/ΔC) of 2.4% (Day 48, p<0.05). At the dose of 20 mg/kg QD, tumor stasis was achieved and maintained for 48 days. The 10 mg/kg QD dose was also significantly efficacious (ΔT/ΔC=25%, p<0.05), while the 1 and 3 mg/kg QD doses were not significantly effective (%ΔT/ΔC of 51% and 56%, respectively). Tamoxifen and fulvestrant, used as controls, induced tumor stasis and a suppression of growth, respectively.

Example 4

ER+ Primary Breast Cancer Model HBRX1298 in NSG Mice

Figure 5:
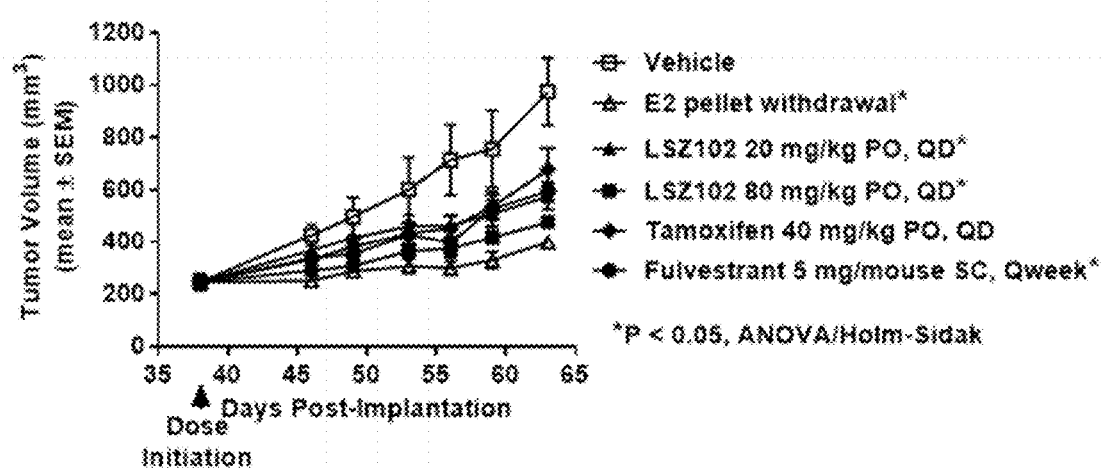
FIG. 5: Anti-tumor efficacy of LSZ102, fulvestrant and tamoxifen in the primary human breast cancer HBRX1298 xenograft model.

The ER+ primary breast cancer model HBRX1298, which is sensitive to estrogen, was tested in NSG mice under the following conditions: LSZ102 20 mg/kg PO QD, LSZ102 80 mg/kg PO QD, tamoxifen 40 mg/kg PO QD, fulvestrant 5 mg/mouse SC, weekly, vehicle control and control with estradiol timed-release pellet removal (FIG. 5). The effect of the treatments on tumor response in the HBRX1298 breast cancer xenograph model on Day 63 are presented in Table 3.

TABLE 3

| Test agent | Dose, Schedule | Tumor response ΔT/ΔC (%) |
|---|---|---|
| Vehicle | None PO, QD | 100 |
| Vehicle, but with Estradiol pellet removal | None PO, QD | 21* |
| LSZ102 | 20 mg/kg PO, QD | 45* |
| LSZ102 | 80 mg/kg PO, QD | 32* |
| Tamoxifen | 40 mg/kg PO, QD | 59 |
| Fulvestrant | 5 mg/mouse SC, QWeek | 48* |

*p < 0.05 versus vehicle (One-way ANOVA/Holm-Sidak post-hoc test).

HBRX1298 tumors were established in NSG female mice by injection of a tumor brei into the inguinal mammary fat pad area. Mice were implanted with 0.72 mg estradiol/90-day release pellets several days prior to cell implantation.

When tumors reached approximately 250 mm3, mice were randomized according to tumor volume into treatment groups (n=6 for all, except n=4 for estradiol withdrawal) on Day 38. There was an efficacy benefit at doses of 20 and 80 mg/kg QD of LSZ102. The 80 mg/kg QD dose of LSZ102 showed statistically significant efficacy over vehicle treated controls and comparable efficacy to that seen in mice with estradiol pellet removal. The 80 mg/kg QD dose inhibited tumor volumes close to the extent observed in mice with estradiol pellet removal (%ΔT/ΔC=32% and 21%, respectively; p<0.05).

Example 5

Y537S ER Mutant MCF-7 Breast Cancer Model in NSG Mice

Figure 6:
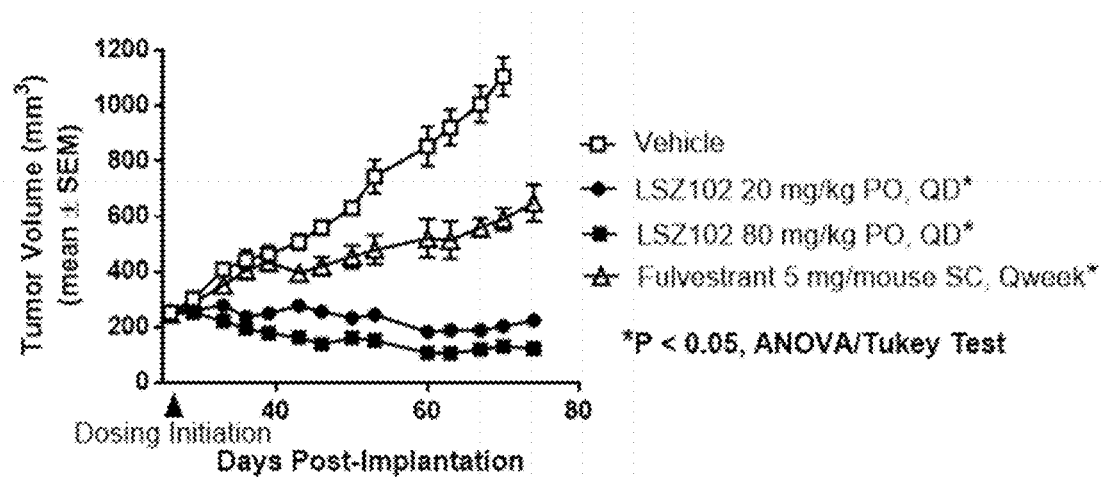
FIG. 6: Efficacy of LSZ102 and fulvestrant in the Y537S ER mutant MCF-7 breast cancer xenograft model.

The Y537S ER mutant MCF-7 breast cancer model was tested in NSG mice under the following conditions: LSZ102 20 mg/kg PO QD, LSZ102 80 mg/kg PO QD, fulvestrant 5 mg/mouse SC weekly, and vehicle control (FIG. 6). The effect of the treatments on tumor response in the Y537S ER mutant MCF-7 breast cancer model on Day 70 are presented in Table 4.

TABLE 4

| | | Tumor response | |
|---|---|---|---|
| Test agent | Dose, Schedule | ΔT/ΔC (%) | Regression (%) |
| Vehicle | None PO, QD | — | — |
| LSZ102 | 20 mg/kg, QD, PO | −5.5 | 17.7 |
| LSZ102 | 80 mg/kg, QD, PO | −13.9 | 46.9 |
| Fulvestrant | 5 mg/mouse SC, QWeek | 39.4 | none |

*p < 0.05 versus vehicle (One-way ANOVA/Tukey post-hoc test).

The MCF-7 cell line was engineered using CRISPR technology to knock out the innate wild type functional ER and knock-in mutant Y537S ER. Ovariectomized female NSG mice were implanted with 10×10⁶ cells in 50% Matrigel® into the axillary mammary fat pad area of each mouse. When tumors reached an average of 250 mm³, mice were randomized according to tumor volume into treatment groups.

Daily LSZ102 treatment at 20 and 80 mg/kg regressed the Y537S ER expressing MCF-7 xenografts demonstrating activity in breast cancers expressing this mutant form of ER, while fulvestrant did not reach statistically significant efficacy.

Example 6

D538G ER Mutant MCF-7 Breast Cancer Model in NSG Mice

Figure 7A:
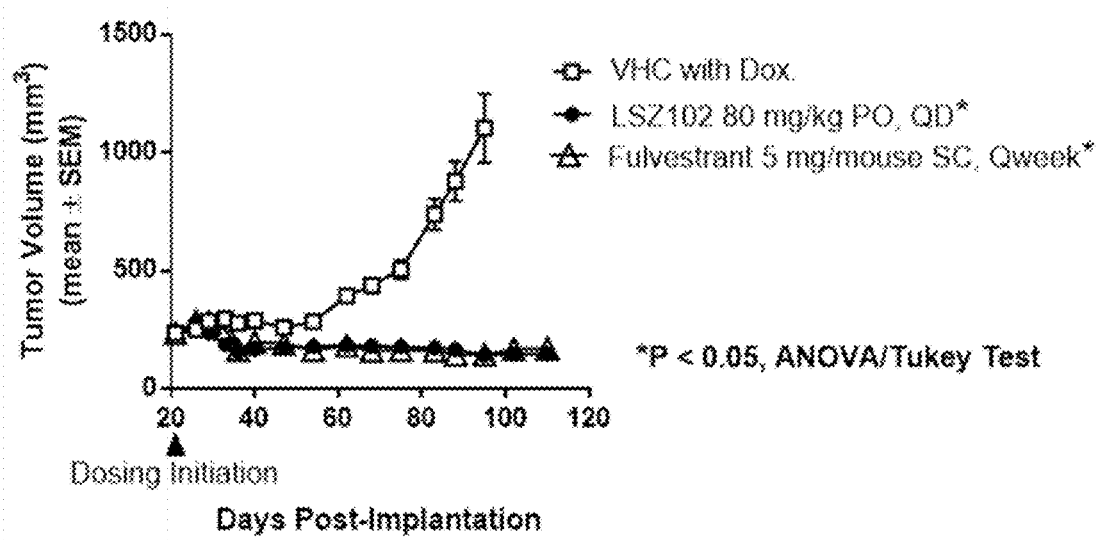
FIG. 7A: Efficacy of LSZ102 and fulvestrant in the D538G ER mutant MCF-7 breast cancer xenograft model.

The D538G doxycycline-inducible ER mutant MCF-7 breast cancer model was tested in NSG mice under the following conditions: LSZ102 80 mg/kg PO QD, fulvestrant 5 mg/mouse SC weekly, and vehicle control (FIG. 7A). The effect of the treatments on tumor response in the D538G ER mutant MCF-7 breast cancer model on Day 74 are presented in Table 5.

TABLE 5

| | | Tumor response | |
|---|---|---|---|
| Test agent | Dose, Schedule | ΔT/ΔC (%) | Regression (%) |
| Vehicle | None PO, QD | — | — |
| LSZ102 | 80 mg/kg, QD, PO | −89.3 | 37.7 |
| Fulvestr%%ant | 5 mg/mouse SC, QWeek | −66.5 | 28.1 |

*p < 0.05 versus vehicle (One-way ANOVA/Tukey post-hoc test).

The MCF-7 cell line was engineered with a doxycycline-induced promoter to express the D538G mutant ER. Ovariectomized female NSG mice were implanted with 10×10⁶ cells in 50% Matrigel® into the axillary mammary fat pad area of each mouse. Eight days after cell implantation, mice received doxycycline via the mouse chow. When tumors reached an average of 250 mm³, mice were randomized according to tumor volume into treatment groups.

Daily 80 mg/kg of LSZ102 regressed the D538G ER expressing MCF-7 xenografts demonstrating activity in breast cancers expressing this mutant form of ER, while fulvestrant was also active.

Figure 7B:
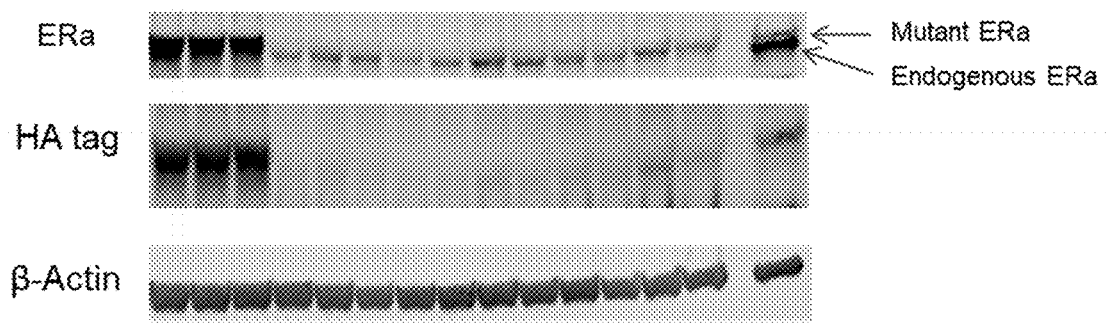
FIG. 7B: ERα degradation activity of LSZ102 and fulvestrant in D538G ER mutant MCF-7 cells.

Protein was isolated from tumors at the end of the efficacy for use in a western blot analysis (FIG. 7B). The membrane was immunostained with an anti-ER or anti-hemagglutinin (HA) antibody since the mutant ER protein was HA tagged. The membrane was also stained for β-actin to serve as a loading control. A set of protein samples from tumors collected after two weeks of dosing with LSZ102 was also included. The samples show degradation of this D538G mutant ER protein.

Example 7

Dose Fractionation Study of LSZ102 in Mice with MCF-7 Xenografts

Figure 8A:
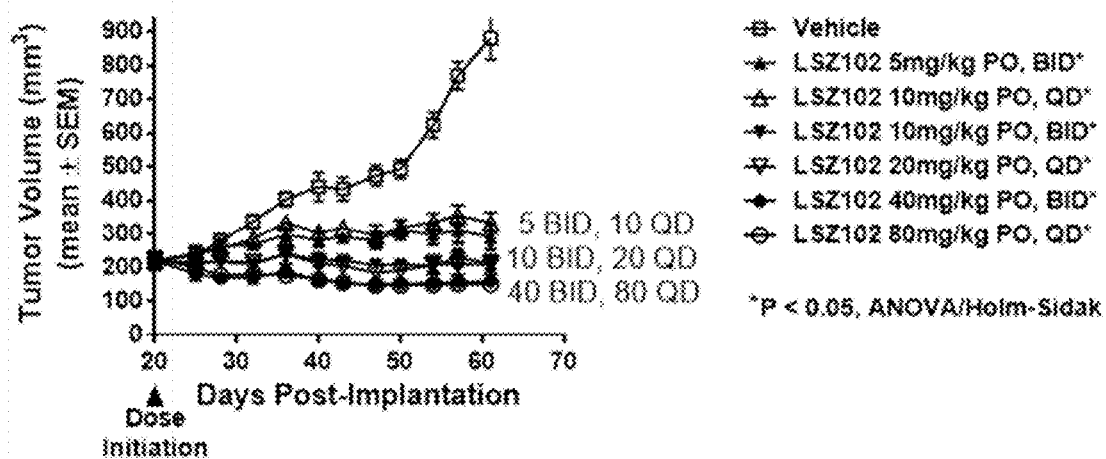
FIG. 8A: Impact of LSZ102 dose fractionation on efficacy in the MCF-7 xenograft model.

A dose fractionation study of LSZ102 in mice with MCF-7 xenografts to assess the effect of QD dosing versus split-dose twice daily (BID) dosing showed equivalent efficacy suggesting that LSZ102 is driven by total exposure (FIG. 8A). The effect of the treatments on tumor response in the MCF-7 breast cancer xenograft model on Day 61 is presented in Table 6.

TABLE 6

| | | Tumor response | |
|---|---|---|---|
| Test agent | Dose, Schedule | ΔT/ΔC (%) | Regression (%) |
| Vehicle | None PO, QD | 100* | — |
| LSZ102 | 5 mg/kg, PO, BID | 11* | — |
| LSZ102 | 10 mg/kg, PO, QD | 16* | — |
| LSZ102 | 10 mg/kg, PO, BID | −1* | — |
| LSZ102 | 20 mg/kg, PO, QD | −2* | 5* |
| LSZ102 | 40 mg/kg, PO, BID | −8* | 21* |
| LSZ102 | 80 mg/kg PO, QD | −11* | 31* |
| Tamoxifen | 60 mg/kg, PO, 5QW | −4* | 11* |
| Fulvestrant | 5 mg/mouse SC, QWeek | 18* | — |

*p < 0.05 versus vehicle (One-way ANOVA/Holm-Sidak post-hoc test).

Figure 8B:
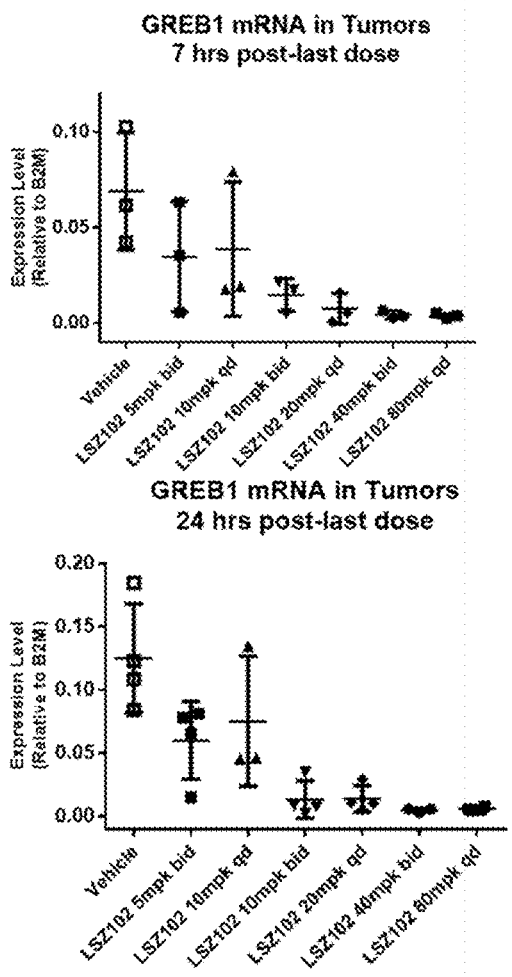
FIG. 8B: Impact of LSZ102 dose fractionation on ER regulated transcripts GREB1 and PGR mRNA levels.
Figure 8B:
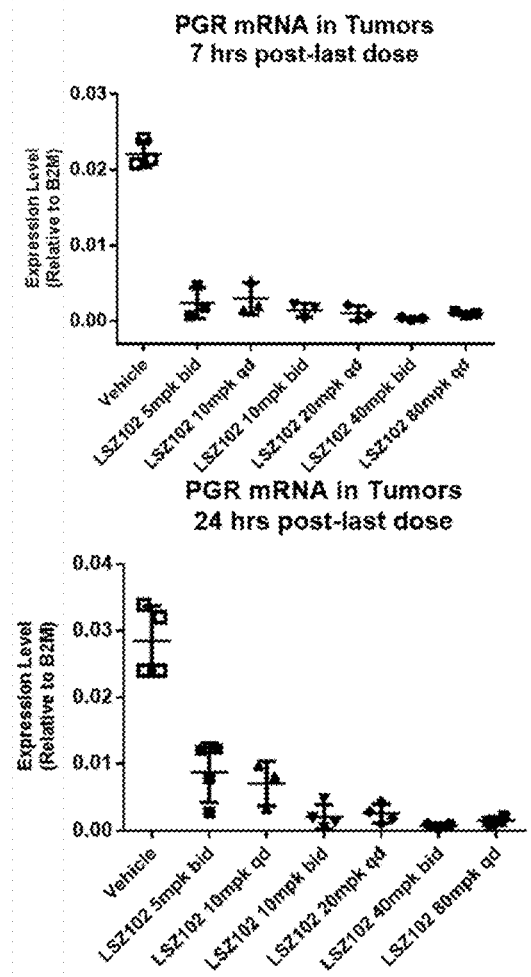

Following a final treatment on day 61, tumors collected after 24 hours showed that the higher dose levels provided slightly stronger inhibition of ER regulated transcripts GREB1 and PGR mRNA levels during the 24 hours dose intervals, but the PD between QD dosing and the BID split dose were the same (FIG. 8B). Data is plotted for individual animals and is normalized to expression of beta-2 microglobulin (B2M).

Example 8

Figure 9:
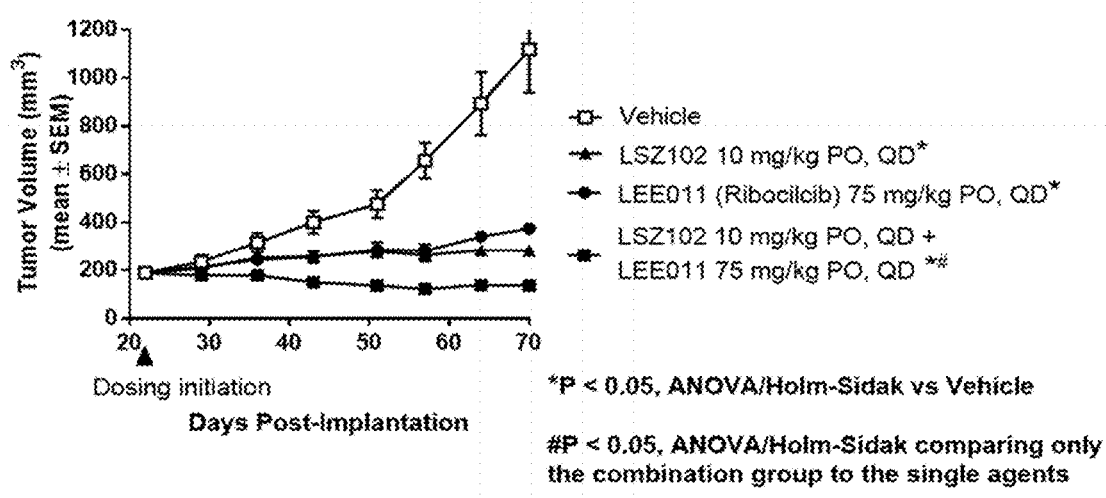
FIG. 9: Anti-tumor efficacy of LSZ102 in combination with ribociclib (LEE011) in the orthotopic human breast cancer MCF-7 xenograft model.

LSZ102 in Combination with Ribociclib in the ER+ MCF-7 Breast Cancer Model in Mice The efficacy of LSZ102 and ribociclib as a combination was tested in the orthotopic MCF-7 breast cancer model in mice (FIG. 9). Tumor growth inhibition (%ΔT/ΔC of 10% and 19%) was observed in single agent treatments of LSZ102 at 10 mg/kg QD and ribociclib at 75 mg/kg QD, respectively. Surprisingly, the combination of the two induced a 28% tumor regression. The effect of the treatments on tumor response in the MCF-7 breast cancer model on Day 70 is presented in Table 7.

TABLE 7

| Test agent | Dose, Schedule | Tumor response | |
|---|---|---|---|
| | | ΔT/ΔC (%) | Regression (%) |
| Vehicle | None PO, QD | 100 | — |
| LSZ102 | 10 mg/kg, PO, QD | 10* | — |
| LEE011 | 75 mg/kg, PO, QD | 19* | — |
| LSZ102 + LEE011 | 10 mg/kg + 75 mg/kg, PO, QD | −5*# | −28*# |

*$p < 0.05$, One-Way ANOVA, Holm-Sidak post-hoc test, versus vehicle control.
$p < 0.05$, One-Way ANOVA, Holm-Sidak post-hoc test, comparing the combination group to the single agents LSZ102 or LEE011.

Example 9

Combination of LSZ102 with Ribociclib in MCF-7 Cells

Figure 10:
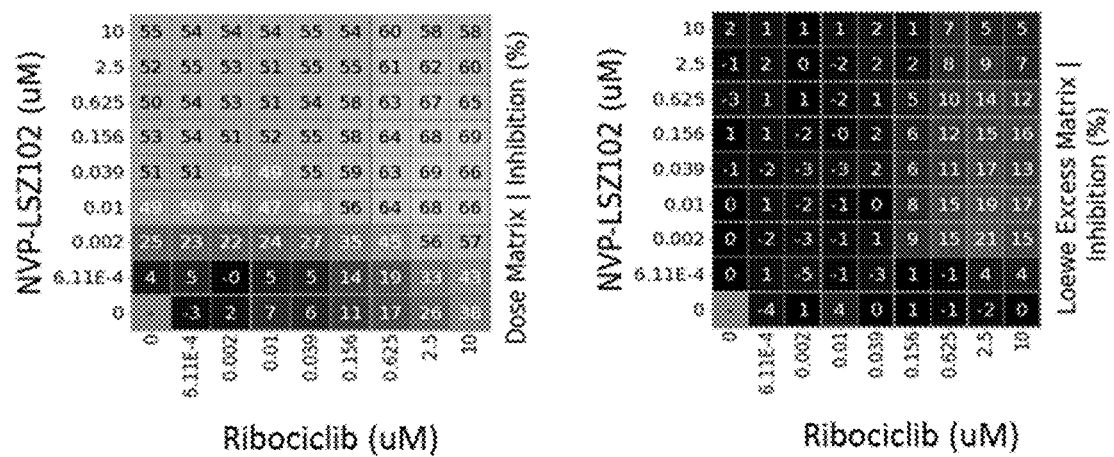
FIG. 10: Dose matrix and isobologram demonstrating the effects of combining LSZ102 with ribociclib on proliferation in MCF-7 cells.

Proliferation assay. MCF-7 cells were cultured in RPMI medium plus 10% full serum media and treated with escalated concentrations of the combined compounds in checkerboard design. Cell viability was determined by CellTiter-Glo assay and normalized to Dimethyl sulfoxide (DMSO) control after 7 days of compound treatment. The percent growth inhibition and excess inhibition were analyzed using the Chalice software (CombinatoRx, Cambridge Mass.). Data was obtained with the Loewe algorithm, which calculates a weighted "Synergy Score" across the dose matrix that adjusts for dose sampling and coverage and weights to favor combination effects at high inhibition levels (Lehar et al. 2009). Synergy score and isobolograms were generated to quantify the combination strength (FIG. 10). A synergy score higher than 2 was considered as significant when compared to the variation of synergy scores seen within self-crosses (drug-with-self; theoretical synergy score of 0) (Lehar et al. 2009). Excess inhibition was calculated using the Loewe synergy model which measures the effect on growth relative to what would be expected if two drugs behave in a dose additive manner Positive numbers represent areas of increasing synergy. Synergistic anti-proliferative effects was observed with the combination of LSZ102 and Ribociclib (synergy score=3.8) in MCF-7 cells in vitro. These results solidly support the potential role for the combination of LSZ102 and Ribociclib in the treatment of ER positive breast cancer.

Example 10

A Phase I/Ib Study of LSZ102±Ribociclib in Patients with Advanced or Metastatic ER+ Breast Cancer The primary objective is to: characterize the safety and tolerability with primary endpoints that include dose limiting toxicities (DLTs) and adverse events (AE); and identify a recommended dose and regimen of LSZ102 alone and/or in combination with ribociclib. Secondary objectives are to evaluate preliminary anti-tumor activity and looking at overall response rate (ORR), duration of response (DOR), progression-free survival (PFS), disease control rate (DCR), pharmacokinetics (PK) and pharmacodynamics (PD).

Eligible patients, ≥18 years old, have histologically confirmed ER+ breast cancer that has progressed after endocrine therapy for metastatic or locally advanced disease or recurrence while on, or within 12 months of the end of adjuvant treatment with an aromatase inhibitor.

All patients in the study were treated with LSZ102 under fasted conditions. In the dose escalation part of the study, patients received once-daily (QD) oral LSZ102 at a starting dose of 200 mg, and subsequent doses of 400 mg, 450 mg, 600 mg, and 900 mg in a single-agent dose escalation arm. As of Aug. 28, 2017, 45 patients had been treated in the following dose groups: LSZ102 200 mg QD (n=4), 400 mg QD (n=6), 450 mg QD (n=13), 600 mg QD (n=16), and 900 mg QD (n=6). Median age was 60.0 years, 67% had ECOG performance status of zero, and 60% had received prior fulvestrant therapy. As of Aug. 28, 2017, 34/45 (76%) patients had discontinued treatment, mainly (31/34 patients) due to progressive disease. The baseline characteristics of these patients and disposition are detailed in tables 8 and 9, respectively, below.

TABLE 8

| Demographic Variable | LSZ102 200 mg QD n = 4 | LSZ102 400 mg QD n = 6 | LSZ102 450 mg QD n = 13 | LSZ102 600 mg QD n = 16 | LSZ102 900 mg QD n = 6 | LSZ102 200-900 mg QD All Patients N = 45 |
|---|---|---|---|---|---|---|
| Age (years) | | | | | | |
| Median (range) | 59.5 (52-69) | 52.0 (41-72) | 64.0 (36-77) | 59.0 (30-73) | 60.5 (49-71) | 60.0 (30-77) |
| ECOG PS, n (%) | | | | | | |
| 0 | 3 (75) | 4 (67) | 4 (31) | 13 (81) | 6 (100) | 30 (67) |
| 1 | 1 (25) | 2 (33) | 6 (46) | 3 (19) | 0 | 12 (27) |

TABLE 8-continued

| Demographic Variable | LSZ102 200 mg QD n = 4 | LSZ102 400 mg QD n = 6 | LSZ102 450 mg QD n = 13 | LSZ102 600 mg QD n = 16 | LSZ102 900 mg QD n = 6 | LSZ102 200-900 mg QD All Patients N = 45 |
|---|---|---|---|---|---|---|
| Unknown | 0 | 0 | 3 (23) | 0 | 0 | 3 (7) |
| Visceral metastases, n (%) | 2 (50) | 3 (50) | 11 (85) | 12 (75) | 6 (100) | 34 (76) |
| Prior lines of therapy, n | | | | | | |
| Median (range) | 4.0 (1-11) | 7.5 (3-10) | 7.0 (3-10) | 5.5 (2-12) | 5.5 (2-11) | 6.0 (1-12) |
| Prior therapy, n (%) | | | | | | |
| Endocrine | 4 (100) | 6 (100) | 13 (100) | 16 (100) | 6 (100) | 45 (100) |
| Fulvestrant | 1 (25) | 5 (83) | 9 (69) | 7 (44) | 5 (83) | 27 (60) |
| CDK4/6 inhibitor | 2 (50) | 3 (50) | 8 (62) | 8 (50) | 3 (50) | 24 (53) |

TABLE 9

| Demographic Variable | LSZ102 200 mg QD n = 4 | LSZ102 400 mg QD n = 6 | LSZ102 450 mg QD n = 13 | LSZ102 600 mg QD n = 16 | LSZ102 900 mg QD n = 6 | LSZ102 200-900 mg QD All Patients N = 45 |
|---|---|---|---|---|---|---|
| Patients treated, n (%) | | | | | | |
| Ongoing | 0 | 1 (17) | 5 (38) | 4 (25) | 1 (17) | 11 (24) |
| Discontinued | 4 (100) | 5 (83) | 8 (62) | 12 (75) | 5 (83) | 34 (76) |
| Reason for discontinuation, n (%) | | | | | | |
| Adverse event | 0 | 0 | 0 | 1 (6) | 0 | 1 (2) |
| Progressive disease | 4 (100) | 5 (83) | 7 (54) | 10 (63) | 5 (83) | 31 (69) |
| Subject/guardian decision | 0 | 0 | 1 (8) | 1 (6) | 0 | 2 (4) |

Dose-limiting toxicities (DLTs) were gastrointestinal disorders that occurred in the LSZ102 600 mg QD (vomiting; n/N=1/16 [6%]) and 900 mg QD (diarrhea; n/N=2/6 [33%]) groups. No DLTs were reported in the 23 patients in the 200-450 mg QD dose groups.

The most common (≥25%) drug-related adverse events (AEs) were diarrhea (62%), nausea (56%), and vomiting (27%; Table 3). Drug-related Grade (Gr) 3 AEs were rarely reported: diarrhea (3 patients [7%]), nausea (2 patients [4%]), vomiting and anemia (both 1 patient [2%]), and no drug-related Gr 4 AEs were reported (Table 10).

A total of 6/45 patients (13%) required dose reduction; this included 4 patients receiving LSZ102 900 mg QD (Gr 3 diarrhea in 2 patients, Gr 2 nausea in 1 patient, and Gr 3 nausea in 1 patient), 1 patient receiving LSZ102 600 mg QD (Gr 3 vomiting) and 1 patient receiving LSZ102 450 mg QD (Gr 2 nausea and Gr 2 vomiting).

TABLE 10

| | LSZ102 QD Dose (Fasted) | | | | | | | | |
|---|---|---|---|---|---|---|---|---|---|
| Preferred | 200 mg n = 4 | | | 400 or 450 mg* n = 19 | | | 600 mg n = 16 | | |
| Term, n (%) | Gr 1 | Gr 2 | Gr 3 | Gr 1 | Gr 2 | Gr 3 | Gr 1 | Gr 2 | Gr 3 |
| Diarrhea | 2(50) | 0 | 0 | 7(37) | 2(11) | 1(17) | 8(50) | 2(13) | 0 |
| Nausea | 2(50) | 0 | 0 | 5(26) | 2(11) | 0 | 9(56) | 1(6) | 1(6) |
| Vomiting | 0 | 0 | 0 | 2(11) | 1(5) | 0 | 5(31) | 0 | 1(6) |
| Decreased appetite | 1(25) | 0 | 0 | 1(5) | (5) | 0 | 3(19) | 0 | 0 |
| Constipation | 0 | 0 | 0 | 2(11) | 0 | 0 | 2(13) | 0 | 0 |
| Dyspepsia | 0 | 0 | 0 | 1(5) | 0 | 0 | 2(13) | 0 | 0 |
| Fatigue | 0 | 0 | 0 | 0 | 1(5) | 0 | 2(13) | 0 | 0 |
| Vaginal discharge | 0 | 0 | 0 | 2(11) | 0 | 0 | 2(13) | 0 | 0 |
| Flatulence | 0 | 0 | 0 | 2(11) | 0 | 0 | 1(6) | 0 | 0 |
| Headache | 0 | 0 | 0 | 1(5) | 0 | 0 | 2(13) | 0 | 0 |

TABLE 10-continued

| | LSZ102 QD Dose (Fasted) | | | | | | | | |
|---|---|---|---|---|---|---|---|---|---|
| Preferred | 200 mg n = 4 | | | 400 or 450 mg* n = 19 | | | 600 mg n = 16 | | |
| Term, n (%) | Gr 1 | Gr 2 | Gr 3 | Gr 1 | Gr 2 | Gr 3 | Gr 1 | Gr 2 | Gr 3 |
| Hot flush | 0 | 0 | 0 | 2(11) | 0 | 0 | 1(6) | 0 | 0 |
| Anemia | 0 | 0 | 0 | 0 | 0 | 1(17) | 0 | 0 | 0 |

*Safety data for 400 and 450 mg doses were combined based on similar PK profiles. A patient with multiple occurrences of a DLT under one treatment is counted only once in the adverse event category for that treatment. A patient with multiple DLTs within a primary system organ class is counted only once in the total row.

A total of 6 patients remained on study treatment for >6 months; of these, 5 patients had received prior treatment with fulvestrant. One patient, whose tumor harbored an ESR1 D538G mutation, had received 9 prior lines of therapy, including fulvestrant for 120 days prior to progression, and letrozole+palbociclib for 94 days prior to progression.

Preliminary evidence of anti-tumor activity was observed with single-agent LSZ102, with a disease control rate of 33%, Table 11.

TABLE 11

| | LSZ102 QD Dose (Fasted) | | | | |
|---|---|---|---|---|---|
| Parameter, n (%) | 200 mg n = 4 | 400 or 450 mg n = 19 | 600 mg n = 16 | 900 mg n = 6 | All Patients N = 45 |
| Complete response (CR) | 0 | 0 | 0 | 0 | 0 |
| Partial response (PR) | 0 | 0 | 0 | 0 | 0 |
| Stable disease (SD) | 3 (75) | 5 (26) | 3 (19) | 3 (50) | 14 (31) |
| Non-CR/Non-PD | 0 | 0 | 1 (6) | 0 | 1 (2) |
| Progressive disease (PD) | 1 (25) | 9 (50) | 8 (50) | 3 (50) | 21 (47) |
| Unknown | 0 | 5 (26) | 4 (25) | 0 | 9 (20) |
| ORR | 0 | 0 | 0 | 0 | 0 |
| DCR | 3 (75) | 5 (26) | 4 (25) | 3 (50) | 15 (33) |

Preliminary PK parameters demonstrate that LSZ102 was rapidly absorbed (median $T_{max}$ 2-3 h). Geomean accumulation half-life was observed to be 5-11 h. Single-agent LSZ102 exposure appears to increase dose-proportionally. AUC and $C_{max}$ were generally comparable on Day 1 and steady state, suggesting absence of drug accumulation. Exposure levels were well in excess of the preclinical efficacious exposure in MCF-7 mouse xenograft models of 3510 h*ng/mL at a dose of LSZ102 20 mg/kg. LSZ102 exposure achieved at all dose levels exceeds the efficacious exposure in preclinical models. A candidate fasted recommended dose for expansion (RDE) of 600 mg QD has been identified, and ongoing studies are further exploring the effect of food on LSZ102 PK. Clinical data (n=7 pairs) has shown an increase in exposure with food where the median AUC increase is 1.7 fold.

Oral single-agent LSZ102 appears well tolerated, with a manageable safety profile. Preliminary evidence of anti-tumor activity was seen in heavily pretreated patients with ER+ breast cancer, including in patients previously treated with fulvestrant and CDK4/6 inhibitors. Six patients remained on study treatment for >6 months, all of whom received ≥6 lines (range 6-11 lines) of prior therapy.

Clinical trials are ongoing for the combination of LSZ102 and ribociclib wherein ribociclib is administered orally (fasted) at 300 mg for 21 days followed by 7 days off treatment in combination with 200 mg (n=5) or 400 mg (n=5) or 600 mg (n=4) of LSZ102. A higher (400 mg) dose of ribociclib is administered orally (fasted) at for 21 days followed by 7 days off treatment in combination with 400 mg (n=4) of LSZ102. Data as of 9 Oct. 2017. In addition, ribociclib is being administered orally (fasted) at 300 mg (n=6) in combination with 450 mg of LSZ102. Based on clinical data, the combination is well tolerated and active.

It is understood that the Examples and embodiments described herein are for illustrative purposes only and that various modifications or changes in light thereof will be suggested to persons skilled in the art and are to be included within the spirit and purview of this application and scope of the appended claims.

What is claimed is:

1. A pharmaceutical combination comprising (E)-3-(4-((2-(2-(1,1-difluoroethyl)-4-fluorophenyl)-6-hydroxybenzo[b]thiophen-3-yl)oxy)phenyl)acrylic acid, or pharmaceutically acceptable salt thereof, and 7-cyclopentyl-N,N-dimethyl-2-((5-(piperazin-1-yl)pyridin-2-yl)amino)-7H-pyrrolo[2,3-d]pyrimidine-6-carboxamide, or a pharmaceutically acceptable salt thereof.

2. A pharmaceutical composition comprising the pharmaceutical combination according to claim 1 and at least one pharmaceutically acceptable carrier.

3. The pharmaceutical combination of claim 1 wherein (E)-3-(4-((2-(2-(1,1-difluoroethyl)-4-fluorophenyl)-6-hydroxybenzo[b]thiophen-3-yl)oxy)phenyl)acrylic acid, or a pharmaceutically acceptable salt thereof, and 7-cyclopentyl-N,N-dimethyl-2-((5-(piperazin-1-yl)pyridin-2-yl)amino)-7H-pyrrolo[2,3-d]pyrimidine-6-carboxamide, or a pharmaceutically acceptable salt thereof, are in the same formulation.

4. The pharmaceutical combination of claim 1 wherein (E)-3-(4-((2-(2-(1,1-difluoroethyl)-4-fluorophenyl)-6-hydroxybenzo[b]thiophen-3-yl)oxy)phenyl)acrylic acid, or a pharmaceutically acceptable salt thereof, and 7-cyclopentyl-N,N-dimethyl-2-((5-(piperazin-1-yl)pyridin-2-yl)amino)-7H-pyrrolo[2,3-d]pyrimidine-6-carboxamide, or a pharmaceutically acceptable salt thereof, are in separate formulations.

5. The pharmaceutical combination of claim 1, wherein the combination is for simultaneous or sequential administration.

* * * * *